United States Patent [19]
Bolinger et al.

[11] Patent Number: 5,204,104
[45] Date of Patent: Apr. 20, 1993

[54] PHYSICAL THERAPY MASSAGE STICK AND PROCESS

[75] Inventors: Robert W. Bolinger, Escondido; Don C. Atkins, Jr., Los Alamitos, both of Calif.

[73] Assignee: Pre Pak Products, Carlsbad, Calif.

[21] Appl. No.: 772,438

[22] Filed: Oct. 7, 1991

[51] Int. Cl.$^5$ ............................................. A61K 7/00
[52] U.S. Cl. .................... 424/401; 424/65; 424/66; 424/68; 424/78.02; 424/78.03; 424/DIG. 5; 514/772; 514/772.4
[58] Field of Search ............ 424/401, 78.02, 78.03, 424/DIG. 5, 65, 66, 68; 514/772, 772.4; 252/174

[56] References Cited

U.S. PATENT DOCUMENTS

| | | | |
|---|---|---|---|
| 2,309,722 | 2/1943 | Wilkes et al. | 424/70 |
| 2,626,847 | 1/1953 | Brown | 424/DIG. 5 X |
| 4,137,306 | 1/1979 | Rubino et al. | 424/DIG. 5 X |
| 4,234,450 | 11/1980 | Hirayama et al. | 424/DIG. 5 X |
| 4,239,781 | 12/1980 | Edwards | 424/DIG. 5 X |
| 4,478,853 | 10/1984 | Chaussee | 514/772 |
| 5,124,313 | 6/1992 | Schaeffer et al. | 514/2 |

OTHER PUBLICATIONS

The Dow Chemical Company, "The Polyglycol Handbook", 1988.
Union Carbide Corporation, "CARBOWAX Polyethylene Glycols", 1986.
Amerchol Corporation, "Material Safety Data Sheet—SOLULAN 75", 1991.

*Primary Examiner*—Thurman K. Page
*Assistant Examiner*—Robert H. Harrison
*Attorney, Agent, or Firm*—Juettner Pyle & Lloyd

[57] ABSTRACT

A process for conducting therapeutic deep tissue physical massage on human patients, and an aid for use in practicing the process, are characterized by a solid, massage stick comprised of three polyethylene glycols, namely, a major proportion of a first polyethylene glycol having a relatively high viscosity and a melting temperature in excess of the temperature of the human body, a lower proportion of a second polyethylene glycol having a melting temperature less than the temperature of the human body, and a minor proportion of a third polyethylene glycol exhibiting lubricity or emolliency. The resultant product and use of the same pursuant to the process provide the therapist with a solid firmness and a sense of tackiness or drag needed for effective therapeutic deep tissue massage and mobilization; and at the same time, provide a degree of lubricity or emolliency that mitigates against abrasion or traumatization of the skin and contributes to the massaging actions of the therapist and a feeling of well being on the part of the patient.

5 Claims, No Drawings

PHYSICAL THERAPY MASSAGE STICK AND PROCESS

FIELD OF THE INVENTION

The present invention relates to the art of deep tissue therapeutic massage and particularly to the processes and instrumentalities used by physical therapists in conducting deep tissue, myofacial, scar tissue, connective tissue and trigger point massage and mobilization therapy.

BACKGROUND OF THE INVENTION

In performing physical therapeutic massage, particularly in the treatment of scar tissue, muscle injuries and the like, a physical therapist is required to probe deeply into the affected tissue to massage and mobilize the tissue and return the same to a normal healthy condition. This is customarily done by hand, using the fingers, palm and/or heel of the hand to apply a selected amount of physical pressure over a selected area of the affected tissue. To minimize irritation and abrasion of the skin and superficial tissues overlying the affected tissue, a cream, salve, or lotion is frequently applied to the skin. This however imparts a slip factor at the interface between the hand of the therapist and the body of the patient and tends to reduce rather than enhance the therapist's sensitivity and effectiveness in carrying out the treatment.

Lotions and creams are fine for superficial soft tissue mobilization massage, but they are not generally an affirmative aid to deep tissue and myofacial massage and mobilization.

SUMMARY OF THE INVENTION

The object of the present invention is to provide a process and an instrumentality for use by physical therapists in conducting deep tissue, myofacial, scar tissue and trigger point massage and mobilization that will enhance the therapist's ability to perform the treatment while at the same time reducing patient discomfort and potential incidental traumatization of overlying soft tissues and skin.

More particularly, it is an object of the invention to provide a therapy process and aid that will afford an ideal interface between the hand of the therapist and the body of the patient, and that will supply the feel of lubricity or emolliency desired by the patient and the firmness and the tack or drag coefficient needed by the therapist to facilitate deep penetrating massaging action.

In accordance with the invention, a deep tissue massage aid is provided in the form of a stick comprised of materials which remains essentially solid under conditions of use and which provides a working or massaging surface which upon contact with and at the temperature of the human body affords a massaging surface exhibiting a degree of lubricity, and a tackiness and solid firmness facilitating deep penetrating massaging action.

Further in accord with the invention, the stick of materials is comprised of a mixture of ingredients including a major proportion by weight of a first polyethylene glycol having a relatively high viscosity and a melting temperature above the temperature of the human body, a lower proportion by weight of a second polyethylene glycol having a melting temperature less than the temperature of the human body, and a minor proportion by weight of a third polyethylene glycol exhibiting emolliency; the respective proportions of these ingredients in the composition being such as to impart to the stick the solid firmness and tackiness required for the therapist and the feel of lubricity desired for the patient.

The massage therapy of the invention thereby enhances the therapist's ability to carry out the treatment sensitively and effectively, and at the same time minimizes discomfort to the patient.

These and other objects and advantages of the invention will become apparent from the following detailed description.

DETAILED DESCRIPTION

The following is a detailed description of the best mode presently contemplated by the inventors for carrying out their invention.

In its preferred embodiment, the massage stick of the invention takes the form of a solid cylinder about 1 to 1 ⅛ inches diameter, preferably 1¼ inches in diameter, and is packaged in a conventional tubular container having a removable top cap and a push-up or twist-up bottom wall for advancing the stick above the top edge of the tube as the top marginal portions of the stick are consumed in use. This type of container is widely used in the cosmetics industry for the packaging of stick deodorants and other stick-type cosmetic products. Accordingly, a drawing of the container and the contained product is not deemed necessary to this detailed description, as the visual appearance is quite conventional.

The tubular container may be of any length desired, but for convenience of use, handling and manipulation by a physical therapist, the container is preferably from about 3 to about 5 inches long. As initially supplied to a therapist, the composite massage stick will preferably be of essentially the same length as or slightly shorter than the internal length dimension of the container. The stick and its container may of course take different cross-sectional configurations, e.g, elliptical, and different lengths, as desired.

The stick is formulated from a mixture of ingredients comprised principally of three different polyethylene glycols, namely, a major proportion of a first polyethylene glycol having defined characteristics, including a high viscosity, a lower proportion of a second polyethylene glycol having different desired characteristics, and a minor proportion of a polyethylene glycol exhibiting emolliency, preferably an ethoxylated lanolin.

Polyethylene glycols are well known in the art and comprise polymers of ethylene oxide which can be represented by the general formula $HO(CH_2CH_2O)_nH$, where n represents the average number of ethylene oxide units. They are linear polymers containing two terminal primary hydroxyl groups. Product names are customarily followed by a number indicating their approximate average molecular weight. For example, 200 is a polyethylene glycol of average molecular weight 200.

Differences in the physical properties of polyethylene glycols are due primarily to molecular weight. As molecular weight increases, viscosity and freezing point increase, while solubility in water and organic liquids decreases. Polyethylene glycols in the range of 200 to 600 are clear viscous liquids at room temperatures. Those in the range of 900 to 1500 are white, waxy solids. Those in the range of 3,000 to 8,000 are hard, white, opaque solids. It is known to blend polyethylene glycols together to produce materials of a desired viscosity or texture In the preferred embodiment of the invention, three polyglycols are combined to produce the massage stick of the invention. The first polyethylene glycol is one having an average molecular weight in the order of from about 3,000 to about 3,700, a melting point or temperature in the order of from about 125 degrees F. to about 140 degrees F., a viscosity at 210 degrees F. in the order of about 90–92 centistokes ("cs"), and an average of about 74 to 76 moles of ethylene oxide, i.e., 74 to 76 repeating oxyethylene units. The Cosmetics, Toiletries and Fragrances Association generically denominates this product "PEG-75", i.e., a polyethylene glycol having about 75 moles of ethylene oxide. Suitable PEG-75 products are available from Dow Chemical Company under the trade designation "E3350" and from Union Carbide Corporation under the trademark "Carbowax" followed by the trade designation "PEG3350"—the numeral 3350 in both designations indicating an average molecular weight of 3350, and falling within the range of from about 3,000 to about 3,700. PEG-75 is a hard, white, opaque solid at room temperatures.

The second polyethylene glycol in the preferred embodiment of the invention is one having an average molecular weight in the order of from about 570 to about 630, a melting point or temperature in the order of about 65 to about 80 degrees F., a viscosity at 210 degrees F. in the order of about 10–11 centistokes, and an average of about 12 to 14 moles of ethylene oxide. The Cosmetics, Toiletries and Fragrances Association generically denominates this product "PEG-12". Suitable PEG-12 products are available from Dow Chemical Company under the trade designation "E600" and from Union Carbide Corporation under the trademark "Carbowax" followed by the trade designation "PEG600" —the numeral 600 in both designations indicating an average molecular weight of 600, and falling within the range of from about 570 to about 630. PEG 12 is a clear viscous liquid at room temperatures.

The third ingredient of the preferred embodiment of the massage stick of the invention is an ethoxylated lanolin, i.e., a polyethylene glycol derivative of lanolin. The preferred lanolin derivative has in the order of about 75 moles of ethylene oxide and therefore has some characteristics in common with PEG-75. However, the lanolin derivative, which is designated "PEG-75 Lanolin" by the Cosmetics, Toiletries and Fragrances Association, has the skin feel of an emollient and is included in the massage stick for the patient's comfort, i.e., a feeling of emolliency or lubricity. PEG-75 Lanolin is available from Amerchol Corporation, Edison, N.J., under the trademark "SOLULAN-75" or from the Emery Division of Witco Chemical under the trade designation "Ethoxylan 1686". PEG-75 Lanolin is a waxy solid having a light amber color and a faint pleasant order.

In order to provide a massage stick having the necessary firmness, lubricity and tack or drag required by the invention, the three polyethylene glycols must be blended in reasonably precise ratios. In a preferred embodiment, the first, second and third polyethylene glycols are combined in relative percentages by weight in the order of about 54%, 41% and 5% respectively. While minor proportions of other ingredients, for example, fragrances and/or colors, may be added if desired, it is preferred for professional therapeutic massage that the massage stick consist of just the three polyethylene glycols blended in the weight percents stated, i.e., 54%, 41% and 5%. When so blended, 8.33 pounds of the blend will produce 1 gallon of the composition comprising the massage stick of the invention.

The polyethylene glycols are suitably blended under heat in a stainless steel jacketed tank equipped with heating means and a variable speed mixer. The PEG-75 is first charged into the tank and heated until the materials start to melt, i.e., at a temperature in the order of about 125 to 140 degrees F. The PEG 75 Lanolin is then added while the tank continues to be heated and the mixer energized to mix the two polyethylene glycols until the mixture is uniform. The PEG-12 is then added and mixed with the other polyethylene glycols. The temperature should be controlled to keep the temperature of the mix just slightly above its melting point, and mixing is continued until the system is uniform. This mix may then be cooled until it has the consistency of heavy cream, whereupon it may be poured, pumped or otherwise transferred into the massage stick containers. As cooling continues, the polyethylene glycol composition solidifies in the shape of the container, i.e., in the preferred embodiment, a solid cylinder about 1¼ inch in diameter and about 3 to 5 inches long.

The resultant massage stick, when massaged against a human body, has a solid firmness enabling deep penetrating massage and its surface exhibits a certain tackiness or a coefficient of drag that gives the therapist the sense of feel needed to perform physical therapeutic massage and tissue mobilization effectively and with sensitivity. At the same time, the surface of the stick also exhibits a certain degree of lubricity or emolliency that is beneficial to the massaging actions of the therapist, that prevents abrasion of the patient's skin, and that imparts to the patient a nice skin feel and therefore a sense of well being and security. The stick therefore provides an ideal interface between the hand of the therapist and the body of the patient.

The melting temperature of the massage stick may be in the range of from about 100 degrees F. to about 125 degrees F., so that the same will not melt or deteriorate under normal conditions of shipment and storage. In desert climates for example, a melt temperature at the upper end of the range may be required and may, if necessary, be attained by relatively increasing the weight percent of the PEG-75 and reducing the weight percent of the PEG-12. However, to the extent feasible, and specifically in the preferred embodiment of the invention, the melting temperature is kept at or near the lower end of the range, e.g., 104 degrees F., so that the stick will not melt or deteriorate or become soft or lose its overall firmness under conditions of normal use, but will be such that the composition on the working surface of the stick will melt or be transformed and transferred to the skin of the patient during physical therapy thereby to provide both the requisite drag or tack and the desired emolliency.

The objects and advantages of the invention have therefore been shown to be attained in a convenient, economical, and facile manner.

While the preferred embodiment of the invention has been herein described, it will be appreciated that various changes, rearrangements and modifications may be made therein without departing from the scope of the invention, as defined by the appended claims.

What is claimed is:

1. A massage stick for use by physical therapists in conducting tisue mobilization, myofacial and deep tissue massage therapy on patients, comprising a solid stick of ingredients which remains essentially solid at and below the temperature of the human body and which upon contact with and at the temperature of the human body provides a massaging surface exhibiting a degree of lubricity, a degree of tackiness and a solid firmness facilitating deep penetrating massaging action, said stick comprising a composition of ingredients including a major porportion by weight of a first polyethylene glycol having a relatively high viscosity and a melting temperature above the temperature of the human body, a lower porportion by weight of a second polyethylene glycol having a melting temperature less than the temperature of the human body, and a minor porportion by weight of a third polyethylene glycol exhibiting emolliency, said first polyethylene glycol having an average molecular weight of from about 3,000 to about 3,700 and comprising about 54% by weight of said stick, said second polyethylene glycol having an average molecular weight of from about 570 to about 630 and comprising about 41% by weight of said stick, and said third polyethylene glycol comprising an ethoxylated lanolin having in the order of about 75 moles of ethylene oxide and comprising about 5% by weight of said stick.

2. A massage stick as set forth in claim 1 wherein said first polyethylene glycol has an average melting temperature of from about 125 degrees F. to about 140 degrees F., and said second polyethylene glycol has a melting temperature of from about 65 degrees F. to about 80 degrees F.

3. A massage stick as set forth in claim 1 wherein said first, second and third polyethylene glycols form a stick having a melting temperature of from about 100 degrees F. to about 125 degrees F.

4. A massage stick as set forth in claim 1 comprising a solid cylinder having a diameter of from about 1 to about 1¼ inches.

5. A massage stick as set forth in claim 4 including a cylindrical push-up container for said stick, said container having an open top and a push-up bottom so that the top portion of the stick can be pushed upwardly from the container for axial massaging engagement against the body of a patient, said container comprising means for holding and manipulating said stick during therapeutic massage.

* * * * *